United States Patent
Clement et al.

(10) Patent No.: US 9,307,756 B2
(45) Date of Patent: Apr. 12, 2016

(54) PORTABLE RFID TAGGED CARRIER FOR STERILE IMPLANTS AND BIOLOGICAL PRODUCTS

(75) Inventors: Wesley J. Clement, Collierville, TN (US); Steven M. Tethrake, Collierville, TN (US)

(73) Assignee: Warsaw Orthopedic, Inc., Warsaw (IN)

( * ) Notice: Subject to any disclaimer, the term of this patent is extended or adjusted under 35 U.S.C. 154(b) by 156 days.

(21) Appl. No.: 13/281,588

(22) Filed: Oct. 26, 2011

(65) Prior Publication Data

US 2013/0106607 A1    May 2, 2013

(51) Int. Cl.

| | | |
|---|---|---|
| *G08B 13/14* | (2006.01) | |
| *A01N 1/02* | (2006.01) | |
| *G06K 19/077* | (2006.01) | |
| *G06Q 10/08* | (2012.01) | |
| *G06Q 50/22* | (2012.01) | |
| *A61B 10/00* | (2006.01) | |
| *B01L 3/00* | (2006.01) | |

(52) U.S. Cl.
CPC ............ *A01N 1/0273* (2013.01); *A01N 1/0236* (2013.01); *A61B 10/0096* (2013.01); *B01L 3/545* (2013.01); *G06K 19/07758* (2013.01); *G06Q 10/08* (2013.01); *G06Q 50/22* (2013.01); *B01L 2200/147* (2013.01); *B01L 2200/18* (2013.01)

(58) Field of Classification Search
None
See application file for complete search history.

(56) References Cited

U.S. PATENT DOCUMENTS

| | | | |
|---|---|---|---|
| 6,512,459 B2 * | 1/2003 | Benezech et al. ........... | 340/686.4 |
| 6,650,240 B2 * | 11/2003 | Lee et al. ................... | 340/572.1 |
| 7,698,180 B2 | 4/2010 | Fago et al. | |
| 7,838,844 B2 * | 11/2010 | Wagner et al. .......... | 250/432 PD |
| 8,258,961 B2 * | 9/2012 | Phillips et al. ............. | 340/572.8 |
| 2002/0183882 A1 * | 12/2002 | Dearing et al. ............... | 700/115 |
| 2003/0160096 A1 * | 8/2003 | Morimoto ...................... | 235/375 |
| 2004/0233041 A1 * | 11/2004 | Bohman et al. .............. | 340/10.1 |
| 2005/0134433 A1 * | 6/2005 | Sweeney ...................... | 340/10.1 |
| 2006/0109105 A1 | 5/2006 | Varner et al. | |
| 2006/0109106 A1 | 5/2006 | Braun | |
| 2006/0181413 A1 * | 8/2006 | Mostov .................... | 340/539.22 |
| 2007/0216542 A1 | 9/2007 | Brosius et al. | |
| 2008/0184719 A1 * | 8/2008 | Lowenstein .................... | 62/127 |
| 2008/0275287 A1 * | 11/2008 | Stevens et al. ..................... | 588/3 |
| 2009/0061193 A1 * | 3/2009 | Hara et al. ..................... | 428/220 |
| 2009/0109033 A1 | 4/2009 | Salvat | |
| 2009/0109040 A1 * | 4/2009 | MacLean et al. ............. | 340/600 |
| 2009/0128330 A1 | 5/2009 | Monroe | |
| 2009/0212918 A1 | 8/2009 | Bandy et al. | |
| 2009/0268989 A1 | 10/2009 | Berland et al. | |
| 2010/0001848 A1 | 1/2010 | McAllister et al. | |
| 2010/0012653 A1 | 1/2010 | Ulrich et al. | |
| 2010/0066501 A1 | 3/2010 | Ulrich et al. | |
| 2010/0197991 A1 | 8/2010 | Heath | |
| 2012/0025985 A1 * | 2/2012 | Bolander et al. ........... | 340/572.1 |

FOREIGN PATENT DOCUMENTS

WO    2008141936 A1    11/2008

* cited by examiner

*Primary Examiner* — Curtis King

(74) *Attorney, Agent, or Firm* — Sorell Lenna & Schmidt LLP

(57) ABSTRACT

Intelligent portable carrier device for supporting movement in product tracking and monitoring of regulated products, such as tissue and biologics. Embodiments of the invention use product identification technology, such as radio-frequency identification (RFID) tags and readers, to uniquely identify the regulated products as they are added to or removed from the intelligent portable carrier device. Embodiments of the invention may also be configured to monitor and report temperature and other environmental conditions associated with the intelligent portable carrier device.

20 Claims, 2 Drawing Sheets

PORTABLE RFID TAGGED CARRIER FOR STERILE IMPLANTS AND BIOLOGICAL PRODUCTS

BACKGROUND

1. Field of the Invention

The present invention relates to a monitoring system and method, and more particularly, to systems and methods to support improvements in product tracking and monitoring of regulated products such as sterile implants and biological products.

2. Description of the Related Art

In the realm of transporting regulated products such as tissue and biologics, there is a need to track the objects as they are removed from an existing back-end inventory tracking system. One method of tracking the objects while in transport is by using radio frequency identification devices (RFIDS), which are known in the art. Such devices are typically used for inventory tracking.

As regulated products such as sterile implants and biological products are moved in inventory, product manufacturing, and merchandising operations, there is a continuous challenge to accurately track and monitor the location and flow of objects, including temperature, humidity, pH, etc. Additionally, there is a continuing goal to determine the location of objects and the environmental conditions of the products in an inexpensive and streamlined manner.

When regulated products are moved by sales representatives and taken to specific locations, monitoring and tracking of these products will end. Product regulation resumes only when the products are brought back to Smart Storage Sites.

Therefore, what is needed in the art is a system and method for storing, tracking, and transporting stored sensitive regulated products such as sterile implants and other biologic products that overcome the above drawbacks. This would provide real-time inventory and critical monitoring data such as temperature during transport.

SUMMARY

The invention, in various embodiments, addresses deficiencies in the prior art by providing an intelligent portable carrier device, for example a container, that supports movement in product tracking and monitoring of regulated products, such as tissue and biologics. The present invention uses product identification technology, such as radio-frequency identification (RFID) tags and readers to uniquely identify the regulated products as they are added to or removed from the intelligent portable carrier device. A primary, but not exclusive purpose of the intelligent portable carrier device is as a temporary storage process for transportation purposes of sterile and non-sterile medical implants, biologic products, or other RFID enabled materials that require continuous monitoring during transportation.

In various embodiments, the intelligent portable carrier device is provided with a closable opening designed to inventory temporarily stored sensitive items, such as biological materials, provide critical monitoring data, such as temperature monitoring, as well as communicate global positioning system (GPS) location and provide a further capability to transmit the critical monitoring data wirelessly in real time to an existing back-end inventory tracking system using known wireless methods.

A system for monitoring a carrier with a closable opening may comprise: an RFID device; one or more processors configured to monitor and manage certain events related to the temporarily stored sensitive items; a memory for storing monitored data; at least one sensor module; a transmitter for transmitting messages over a wireless network, the messages including modulated information received from the RFID device and the one or more monitoring sensors; a receiving device comprising a receiver for receiving messages transmitted by the RFID device and messages received over the wireless network. At least the information relating to one or more stored sensitive items or conditions sensed by the one or more sensors are processed for providing an indication of the condition of the one or more stored sensitive items.

The event monitoring and event managing processor(s) may be embodied, for example, in one or more software application programs, routines or modules configured to be executed by a general purpose microprocessor, in one or more hardware devices, such as a programmable logic controller (PLC), in one or more firmware devices, or in some combination of software application programs, hardware and/or firmware devices. Typically, although not necessarily, the event monitoring processor (hereinafter referred to as the event monitor) is configured to monitor and detect new events associated with pharmaceutical product containers placed in or near the refrigerator, as well as to monitor and detect new events associated with the refrigerator itself. In some embodiments, the event monitor will generate event codes indicating what type of event has occurred. The event managing processor (hereinafter referred to as the event manager) typically carries out a series of instructions that are appropriate for the particular event that has just occurred. Notably, alternative embodiments of the invention may use fewer or more PLCs, computer software programs, and modules or routines to perform the same functions as the event monitor and event manager. In some embodiments, for example, the functions of the event monitor and the event manager may be performed by the same hardware or software processor.

The intelligent portable carrier device can include common computing and communication technology (such as a microprocessor, digital signal processor, GSM, CDMA and/or WiFi transceiver and so forth) for enabling the intelligent portable carrier device to communicate with common wireless communication systems such as cellular and WiFi base stations.

An exemplary embodiment of the present invention relates to a carrier that is primarily, but not exclusively, used as a temporary storage process for transporting RFID tagged sterile implants and biologic products or other RFID tagged biological materials that require continuous monitoring during transportation.

A particular refinement of the carrier according to an exemplary embodiment of the present invention is characterized in that the carrier provides continuous monitoring of temperature and other environmental factors during transportation.

A particular refinement of the carrier according to an exemplary embodiment of the present invention is characterized in that the carrier is light weight and strong.

A particular refinement of the carrier according to an exemplary embodiment of the present invention is characterized in that interior walls of the carrier are configured to block radio frequency (RF) communications from passing into and out of the carrier.

A particular refinement of the carrier according to an exemplary embodiment of the present invention is characterized in that the carrier is adapted to transmit data wirelessly via WiFi, Zigbee, Blue Tooth, or other known or anticipated wireless methods.

A particular refinement of the carrier according to an exemplary embodiment of the present invention is that it is adapted to augment known advantages of the Smart Storage Inventory Intelligent Portable Carrier Device™ and similar processes, with products that are removed and then transported some distance through the use of a car or currier, to a point of potential use and then back again to a point of origin. For example, a point of origin could be a hospital or a clinic.

According to various embodiments, the present teachings involve methods for providing improved product tracking and monitoring of regulated products, such as sterile implants and biological products in an intelligent portable carrier device comprising a housing, including a lid-closure mechanism, the housing configured to hold the regulated products. The method comprises steps of affixing a product identification tag to at least one regulated product initialized with at least a product ID code unique to the product type and a serial number unique to the specific product or object; placing the at least one tagged regulated product into a carrier; placing the at least one product identification reader into said carrier; scanning the product identification tag with a scanning device to determine the product ID code and serial number; receiving the scanned data from said scanner into a local processor; transmitting said scanned data from said local processor through an electronic data network to a tracking server, and creating a data record on said tracking server to contain said scanned data.

BRIEF DESCRIPTION OF THE DRAWINGS

These and other objects, features and advantages of the present invention will be apparent from a consideration of the following Detailed Description of the invention, when considered in conjunction with the drawing Figures, in which.

DETAILED DESCRIPTION OF THE PREFERRED EMBODIMENTS

Figure 1A:
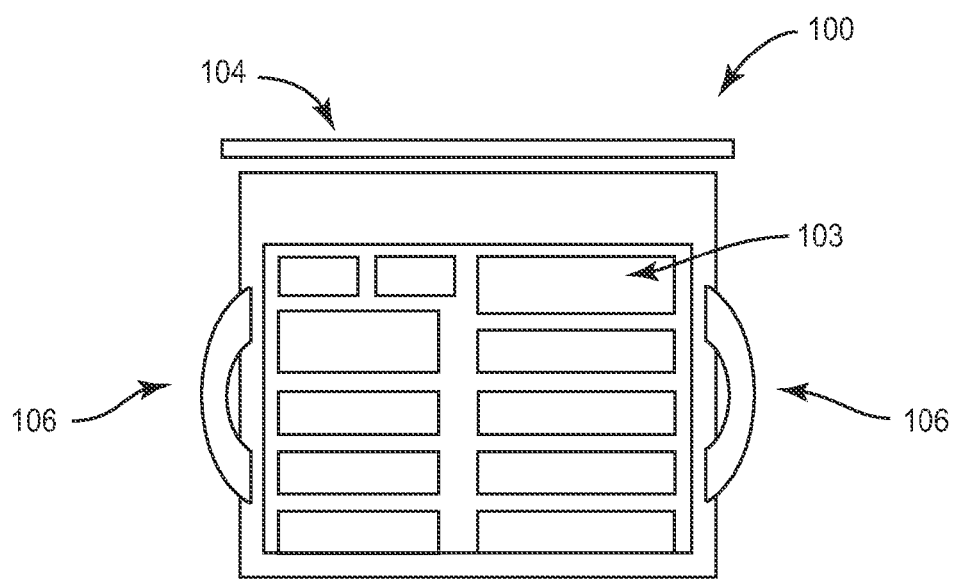
FIGS. 1A and 1B show a front and top view, respectively, of a representative intelligent portable carrier device that is configured for RFD inventory tracking in accordance with one embodiment.

The following description with reference to the accompanying drawings is provided to assist in a comprehensive understanding of exemplary embodiments of the present invention as defined by the claims and their equivalents. It includes various specific details to assist in that understanding but these are to be regarded as merely exemplary. Accordingly, those of ordinary skill in the art will recognize that various changes and modifications of the embodiments described herein can be made without departing from the scope and spirit of the invention. In addition, descriptions of well-known functions and constructions may be omitted for clarity and conciseness.

The terms and words used in the following description and claims are not limited to the bibliographical meanings, but, are merely used by the inventor to enable a clear and consistent understanding of the invention. Accordingly, it should be apparent to those skilled in the art that the following description of exemplary embodiments of the present invention is provided for illustration purpose only and not for the purpose of limiting the invention as defined by the appended claims and their equivalents.

It is to be understood that the singular forms "a," "an," and "the" include plural referents unless the context clearly dictates otherwise. Thus, for example, reference to "a component surface" includes reference to one or more of such surfaces.

Radio Frequency Identification ("RFID") provides a convenient mechanism for identifying and detecting objects using wireless electromagnetic signals. Radio frequency identification (RFID) systems typically include a transceiver and one or more transponders (RFID tags). The transceiver emits radio signals to activate the RFID tags and to read/write data to them via an antenna. The transceiver typically has an associated decoder for decoding data received from an RFID tag. The combination of an antenna, transceiver, and decoder is sometimes referred to as an "interrogator" in an RFID system. The transponder can be electronically programmed with any desirable information, the constraint being size. In a typical RFID system, the interrogator transmits radio waves (range dependent upon power and frequency). When an RFID tag enters the zone in which the interrogator is transmitting, it detects the decoder's activation signal. This causes the RFID tag to transmit its data signal back to the interrogator. RFID tags can be active (i.e., have their own power source for generating the data signal) or passive (i.e., use electromagnetic energy induced in the RFID tag by receipt of the activation signal to generate the data signal). The decoder then decodes the data on the RFID tag. This decoded data is then typically transmitted to a computing system that is in communication with the decoder. An active tag's memory size varies according to application requirements; some systems operate with up to 1 MB of memory.

The RFID reader antenna generates an electromagnetic field, thereby transferring energy to the tag. Depending on the design of the tag, a portion of the energy transferred to the tag will be reflected to the reader so as to provide information about the tag back to the reader. Some RFID systems can be used to read and optionally write data to and from the RFID tag. RFID readers can generate signals spanning distances from less than one inch to more than 100 feet depending on frequency and power of the signals generated at the RFID reader antenna.

As is known in the art, for example from Paratore et al. U.S. Pat. No. 6,294,997, herein incorporated in its entirety, by reference, RFID devices or tags are small, low-cost wireless transponder devices equipped with nonvolatile memory for information storage, typically information about an item or host product to which the RFID tag is attached. For example, inventory items can carry RFID tags providing information such as serial numbers, price, weight, and size. RFID tags are capable of responding to wireless interrogation by wireless transmission of stored information for receipt by the interrogator. The term "RFID tag" is used herein to include self-supporting, self-contained tags, cards or labels that are attachable to a host product or product, continuous web tags separable into individual tags for attachment to a host product, RFIDs supported on a substrate or otherwise constructed for incorporation on or into a host product, and any other RFID device suitable for association with a host product to transmit information regarding the host product externally of the product.

Use of RFID tags can permit efficient retrieval of information regarding an item at various points in the manufacturing and distribution chain, and can also permit tracking of the individual item. Some RFID tags permit relatively large amounts of data to be associated with the product. An RFID tag typically includes a memory, an RF transmitter, an RF receiver, an antenna, and logic for controlling the various components of the memory device. The antenna may be formed on a flexible substrate, while analog RF circuits and digital logic and memory circuits are embodied in an integrated circuit ("IC") carried by the substrate and coupled to the antenna. RFID tags may also include a number of discrete electronic components, such as capacitors, transistors, and diodes.

Passive RFID tags operate without a separate external power source and obtain operating power generated from the reader. Passive tags are consequently typically lighter than active tags, less expensive, and offer a long operational lifetime. Passive tags typically have shorter read ranges than active tags and require a higher-powered reader. Read-only tags are typically passive and can be programmed with a unique set of data (usually 32 to 128 bits) that is typically predetermined at the time of manufacture of the tag. It is understood that passive read/write tags can also be employed consistent with the present teachings.

The term "RFID tag" as used herein refers to either an active or passive RFID tag that contains information. The RFID tag can be read only or read/write, and the information associated with the RFID tag can be hard-coded into the RFID tag at the time of manufacture or at some later time, or the RFID tag can contain information that is written to the RFID tag throughout its lifetime.

The term "RFID reader" as used herein includes RFID devices that can read information from and/or write information into an RFID tag.

RFID devices or tags can take many physical forms, such as a microchip (RFID chip) from 30 to 100 microns thick and from 0.1 to 1 mm across, joined to a minute metal antenna such as the Hitachi 2.45 GHz Mew chip. Another form is the "Coil-on-Chip" system from Maxell (Tokyo, Japan). Exemplary RFID vendors of tags and/or readers and associated systems include Intermec Technologies Corporation (Everett, Wash.), Symbol Technologies (Holtsville, N.Y.), Applied Wireless Identifications, Inc. (AWID) (Monsey, N.Y.), Philips Semiconductor (Eindhoven, The Netherlands), and Texas Instruments (Dallas, Tex.).

In general, RFID chips can include read-only devices (e.g. read-only chips), which include a fixed electronic code. Alternatively, the RFID chips may be read-write devices (e.g. read-write chips), which allow an updating of prior information or an addition of new information. The devices may also be associated with sensors to read detected information and transmit a signal responsive to the detected information, such as a value detected from a biosensor. Exemplary smart tags that include. RFID technology associated with a sensor are the active labels that are commercially available from KSW MICROTEC (Dresden, Germany). For example, TEMPSENS active smart labels can measure and record temperature.

Each individual RFID reader can have an operative power supply and at least one antenna. Optionally, the individual reader may include an antenna group or set having a plurality of antenna. Multiple antennas can, for example, help the reader interrogate and receive data from a diverse selection of tags (or other electronic data mechanisms) where the individual tags have been configured to operate in different, widely-spaced frequencies or frequency bands, such as low-frequency (LF), high-frequency (HF), very-high frequency (VHF), ultra-high frequency (UHF), and super-high frequency (SHF). The operational radio-frequency of the various components of the reader system (e.g. readers, antennas, and communication systems) can be as low as about 100 KHz (kilo-Hertz), and can be up to about 6 GHz (Giga-Hertz) or more.

The reader and/or its antenna system may be powered by conventional techniques and devices. Such techniques and devices can, for example, include capacitors, batteries, photovoltaic cells, electrically-wired power supplies or the like, as well as combinations thereof.

The systems and methods described below are directed to what has been termed herein as RFID carrier applications; however, it will be apparent that the systems and methods described below can be applied to any system in which a plurality of items being tracked or interrogated are located within a confined space. It will also be apparent that certain aspects of the embodiments described below are not necessarily limited to carrier or confined space applications. Thus, it will be understood that the embodiments described below are by way of example only and are not intended to limit the systems and methods described herein to particular applications unless such a limitation is expressly indicated.

Reference will now be made in detail to some embodiments, examples of which are illustrated in the accompanying drawings. Wherever possible, the same reference numbers are used throughout the drawings to refer to the same or like parts.

Figure 1B:
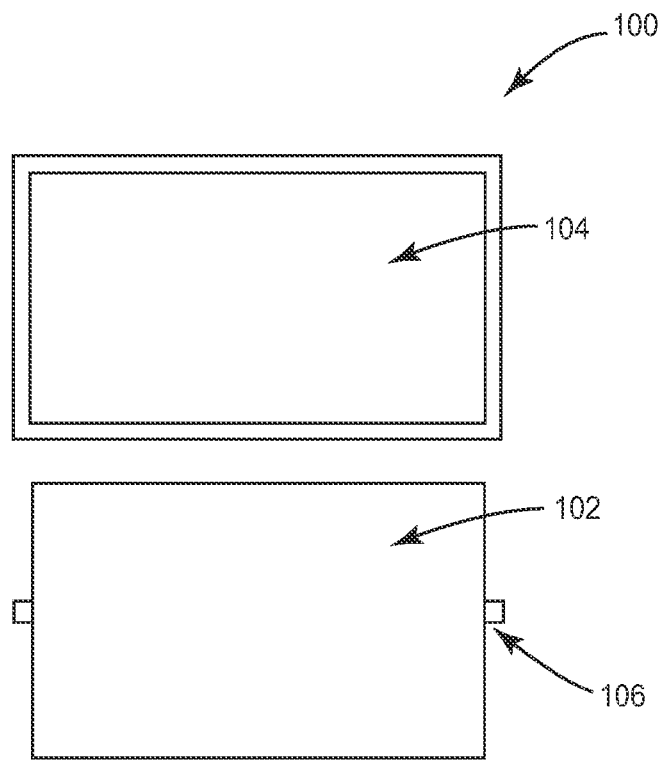

FIGS. 1A and 1B show a front and top view, respectively, of a representative intelligent portable carrier device 100 that is configured for RFID inventory tracking in accordance with one embodiment. Intelligent portable carrier device 100 can be configured to track a plurality of stored sensitive items 103 such as tissue and biologic products, or any other stored sensitive items. Intelligent portable carrier device 100 comprises a shell 102 with a lid-closure mechanism 104 and carrying handles 106. The intelligent portable carrier device 100 is shown in a closed condition in FIG. 1A and in an open condition in FIG. 1B. The shell 102 of the intelligent portable carrier device 100 is constructed to completely contain any RF emitted energy during operation and will not emit outside the intelligent portable carrier device 100 or receive external energy that will impact operation. The shell is preferably made of carbon fiber or other RF absorptive, strong, lightweight materials.

It should be readily appreciated that any suitable article or other commodity may be transported by the intelligent portable carrier device 100 in addition to regulated products. For example, the selected article or commodity may include a liquid, solid, gel, powder, food item, non-food item, compressed item or the like, as well as combinations thereof.

Figure 2:
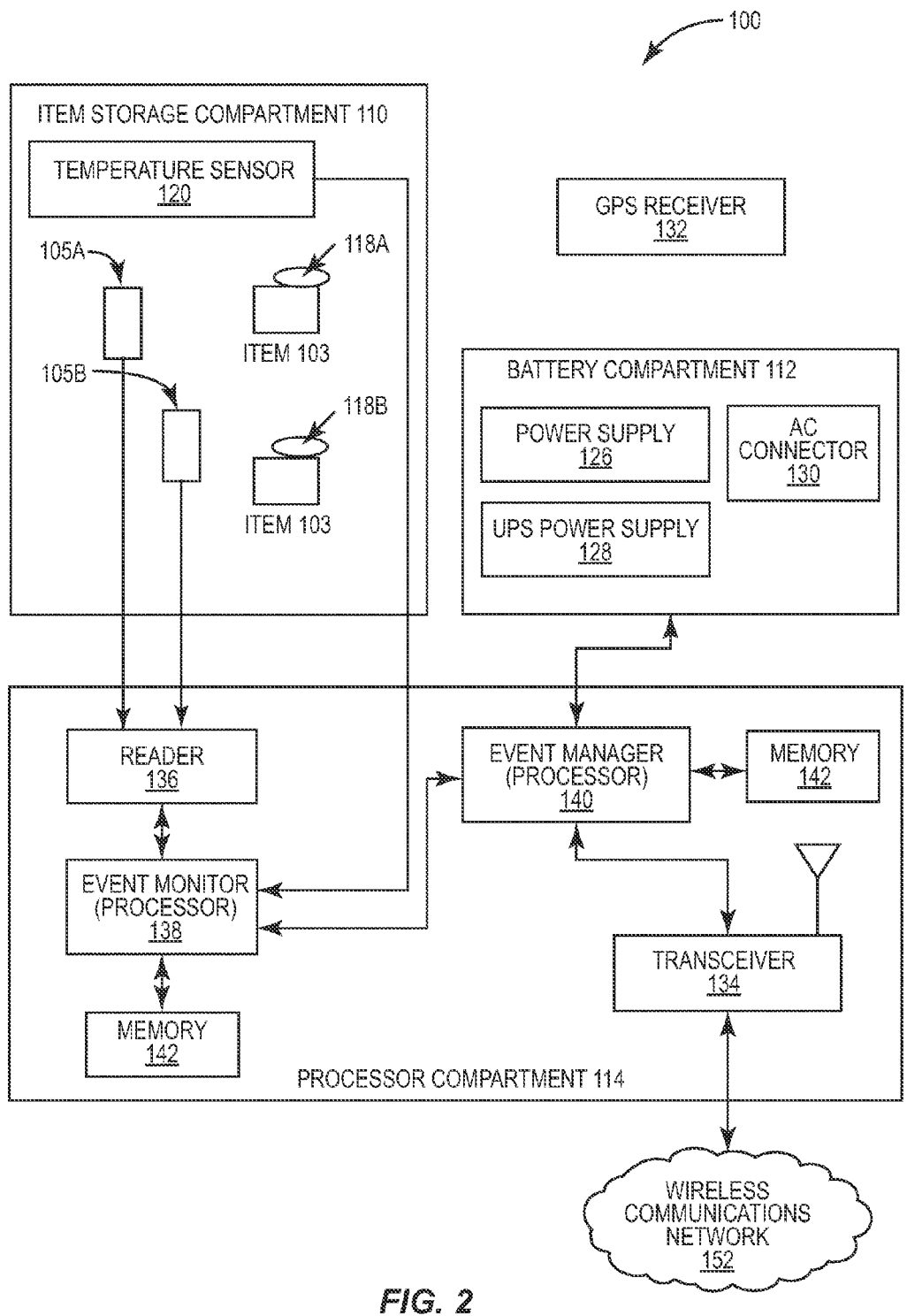
FIG. 2 is a high level block diagram depicting an illustrative embodiment of the major functional components of an intelligent portable carrier device in accordance with an embodiment of the invention.

FIG. 2 is a high level block diagram depicting an illustrative embodiment of the major functional components of an intelligent portable carrier device 100 in accordance with an embodiment of the invention. As shown in FIG. 2, the intelligent portable carrier device 100 generally comprises an item storage compartment 110, a battery compartment 112, and a processor compartment 114. The item storage compartment 110 generally comprises one or more stored sensitive items 103, two of which are shown by way of example, to be transported from a first location to a second location. The stored sensitive items 103 are embedded with product identification tags (e.g., RFID transponders or tags) 118A, 118B, configured to transmit self-identifying signals. Positioned near or within the item storage compartment 110 are antennas 105A and 105B, which may be RFID antennas, which are configured so that their radio-frequency reception ranges (or "read zones") encompass any RFID transponder or tag placed within the item storage compartment 110. Consequently, when stored sensitive items 103 are placed within the item storage compartment 110, antennas 105A and 105B will detect the self-identifying radio frequency signals generated by the transponders attached to or embedded in the stored sensitive items 103.

Item storage compartment 100 also includes a temperature sensor 120 (such as a thermometer), which is positioned to monitor the temperature in the item storage compartment 110. Although FIG. 2 illustrates only one temperature sensor 120, it is noted that embodiments of the invention may utilize a multiplicity of sensors for detecting various environmental conditions in addition to temperature, such as, for example, humidity, pressure and the like.

Also shown in FIG. 2 is a battery compartment 112. In various embodiments, the battery compartment may include a power supply 126, which can utilize common power management technologies (such as replaceable batteries, supply regulation technologies, and charging system technologies) for supplying energy to the components of the intelligent portable carrier device 100 to facilitate portability. There is also shown an uninterruptible power supply (UPS) 128, which will be activated whenever the intelligent portable carrier device battery supply requires recharge while in transit. Further capabilities are provided for connecting the carrier device 100 to an external AC power source 130 to power the device or otherwise recharge the power supply 126 and/or the uninterruptible power supply 128.

Processor compartment 114 comprises an RFD reader 136, and a number of processors including an event monitor processor 138 and an event manager processor 140. Processor compartment 114 further comprises network interface. RFID Reader 136 is an event-driven RFID reader, whose primary function is to collect, decode and pass on information transmitted to the antennas 105A and 105B by the RFID transponders or tags 118A and 118B attached to the one or more stored sensitive items 103. The event monitor processor 138 and event manager processor 140 can utilize computing technologies such as a microprocessor and/or digital signal processor (DSP) with associated storage memory such a Flash, ROM, RAM, SRAM, DRAM, or other like technologies.

RFID Reader 136 typically passes the unique identifier encoded in the self-identifying signals detected by antennas 105A and 105B to event monitor processor 138. Event monitor processor 138 comprises a decision-making software program or programmable logic controller configured to react to the presence, absence, addition, or removal of the self-identifying signals from the radio-frequency reception ranges or "read zones" of the antennas tied to the RFID reader 136. Thus, in some embodiments of the present invention, event monitor processor 138 will generate an event-identifying code in response to the RFID reader 136 detecting that a tagged stored sensitive item is currently located inside or has been added to or removed from a compartment of the intelligent portable carrier device 100. Temperature sensor 120 is also tied to event monitor processor 138 so that the event monitor processor 138 can also generate a temperature change-related event code in response to temperature changes in the compartment.

In some embodiments of the invention, the event monitor processor 138 is also coupled to a power fail circuit, which is configured to detect a power failure condition, such as a power outage. When this happens, the event monitor will generate and pass to the event manager a "power failure" event code, which causes the event manager to determine the starting time of the power outage, and then store the power failure event code and the starting time of the power outage in a status log. Preferably, the system is configured to accomplish these tasks on a high priority basis as soon as a drop in power is detected but before the power is depleted. Alternatively, the system may be configured to accomplish these tasks while the system is operating under the support of an emergency temporary power source, such as a battery or uninterruptible power supply (UPS). Such an emergency power source may also be used by the system to power an internal clock designed to keep track of the current time, so long as the power failure condition persists.

While event monitor processor 138 determines what kind of event has occurred, event manager processor 140 selects the course of action to take and carries out the selected course of action. It is the event manager processor 140, for instance, which sounds an alarm whenever the temperature sensor 120 detects an out of range value. The event manager processor 140 may in certain cases utilize network interface 146 to gain access to a remote inventory database (not shown in FIG. 2) via a data communications network 152.

Although FIG. 2 shows event monitor processor 138 and event manager processor 140 as two distinct components, those skilled in the computer arts will recognize that a single hardware, software or firmware component, or alternatively, a multiplicity of distinct hardware, software and firmware components, may be utilized to implement the functions performed by event monitor processor 138 and event manager processor 140, as described herein, without departing from the spirit or the scope of the present invention.

In certain embodiments, the RFID reader 136 can be configured to receive signals over multiple frequencies in order to increase the reception capabilities. For example, due to the nature of passive RFID, reception of a tags back scatter signal on the carrier frequency can be extremely challenging when radiating into a closed chamber. Allowing the receiver to listen on one or multiple harmonics of the carrier frequency can aid the system's reception capability in a closed chamber environment.

It should be appreciated that the functions necessary to implement the various elements of the intelligent portable carrier device 100 architecture may be embodied in whole or in part using hardware or software, or some combination thereof using microprocessors, microcontrollers, digital signal processors, programmable logic arrays, data storage devices, embedded memory, ROM, RAM, FLASH memory, or any other suitable types of hardware and/or software. It is further appreciated that although the functionality of the system architecture is illustrated in FIG. 2 as being implemented within the respective system elements listed above, the system functions may alternatively be implemented in any other suitable arrangement of elements and in any suitable form. For example, the intelligent portable carrier device architecture may include multiple instances of each type of system element operating in a coordinated manner to deliver the required application services.

In addition, it should be understood that the RFID reader 136 includes an RF interrogator and an RF receiver, and that the RF interrogator and the RF receiver may reside in separate units or may be integrated into a single device. Furthermore, when the term "reader" is employed to refer to the function associated with RF tag interrogation, the term "reader" should be understood to correspond to a device that solely performs that function or is integrated with a component that also performs RF reception. Similarly, when the term "reader" is employed to refer to the function associated with RF reception, the term "reader" should be understood to correspond to a device that solely performs that function or is integrated with a component that also performs RF tag interrogation.

The location of the intelligent portable carrier device 100 may be determined utilizing GPS receiver 132. The GPS receiver 132 can utilize common technology for receiving satellite signals from a constellation of satellites to determine a location coordinate of the intelligent portable carrier device 100. Information, including location information, gathered by the intelligent portable carrier device 100, may be stored in an internal memory 142 associated with processor compartment 114 and/or transmitted, either in real-time or upon arrival at a desired destination to a coupled device that may include, for example, a portable computer or a main server of an existing back end inventory tracking system, such as Smart Storage™ or SAP™ where all the information regarding all of the intelligent portable carrier devices being monitored is retained and stored. The existing back-end inventory tracking systems can be accessed by authorized individuals, hospitals, and other entities. The information pertaining to the individual carrier devices, their contents, and locations is utilized to quickly and correctly augment the known advantages of existing inventory tracking systems, such as Smart Storage™. It can also be used to stop contaminated biologics or faulty products in-transit from being delivered or used by the end user.

In one embodiment, subsequent to taking an inventory of all of the items within the intelligent portable carrier device 100 this information is wirelessly transmitted to a server of an existing back-end inventory tracking system via transceiver 134. The back-end inventory tracking system is configured to store the transmitted information. Transmission to the server is accomplished in real-time via transceiver 134 by any well known transmission protocol, such as for example: Wi-Fi, Blue Tooth, Zigbee, COMA system with AGPS (assisted GPS), GPRS, GSM or other known wireless methods. The transceiver 134 can be configured to be Internet capable.

An inventory of the contents of an intelligent portable carrier device 100 enables a medical representative to indicate which items have been removed from transport from an existing back-end inventory tracking system. For example, when an item, such as a biologic, is removed by a medical representative to take to a location for use, all of the product tracking and temperature monitoring is maintained by the intelligent portable carrier device 100 until it is returned to an existing back-end inventory tracking system, such as Smart Storage™ or the item is otherwise assumed used. It is also envisioned that the intelligent portable carrier device 100 can be constructed out of an insulative material so as to maintain a relatively standard temperature within the portable carrier device 100 relative to the atmospheric environment. In one embodiment, the intelligent portable carrier device 100 is wrapped with an insulative material to realize the same affect.

Such embodiments of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments and other embodiments not specifically described herein, will be apparent to those of skill in the art upon reviewing the above description.

While the invention has been shown and described with respect to particular embodiments, it is not thus limited. Numerous modifications, changes and enhancements will now be apparent to the reader.

What is claimed is:

1. An intelligent portable carrier device comprising a housing including a lid-closure mechanism, a storage compartment, a battery compartment and a processor compartment, the housing being constructed of an RF absorptive material and configured such that any RF emitted energy within the housing does not emit outside the housing, the storage compartment comprising a plurality of regulated products disposed therein, the regulated products each comprising a read-write radio-frequency identification (RFID) tag coupled thereto, the read-write RFID tags each comprising a biosensor configured to detect a condition of the storage compartment, the device comprising a RF reader in the processor compartment configured to collect, decode and pass on information relating to the condition of the storage compartment based upon signals from the tags and to detect whether each of the regulated products is currently in the storage compartment or has been added to or removed from the storage compartment based upon signals from the tags.

2. The intelligent portable carrier device of claim 1, wherein the read-write RFID tags are active RFID tags that are coupled to the regulated products before the regulated products are placed inside the carrier device.

3. The intelligent portable carrier device of claim 1, further comprising a global positioning receiver module for receiving signals from a global positioning system (GPS) and determining a location of said intelligent portable carrier device.

4. The intelligent portable carrier device of claim 1, wherein the read-write RFID tags each include a RFID transponder that communicates with the reader and the device further comprises:
   a plurality of antennas interfaced with the reader configured to communicate radio frequency (RF) signals with the RFID transponders; and
   at least one processor in communication with the reader, configured for:
      i. generating event-identifying codes in response to detecting the presence or absence of an RFID tagged regulated product within the device; and
      ii. generating condition related event codes in response to changes in the condition of the storage compartment.

5. The intelligent portable carrier device of claim 1, wherein the housing comprises an insulative material configured to maintain a relatively standard temperature within the housing relative to an atmospheric environment.

6. The intelligent portable carrier device of claim 1, wherein the read-write RFID tags are each configured to update prior information or add new information related to an environmental condition within the housing.

7. The intelligent portable carrier device of claim 1, wherein the biosensors are configured to measure and record a temperature within the housing, the read-write RFID tags each being configured to update prior information or add new information related the recorded temperature such that the recorded temperature can be determined by a RFID reader.

8. The intelligent portable carrier device of claim 1, wherein the condition is temperature and the RF absorptive material is carbon fiber.

9. The intelligent portable carrier device of claim 1, wherein the regulated products are selected from a group consisting of sterile implants and biologics.

10. A method for providing improved product tracking and monitoring of regulated products, the method comprising:
   providing an intelligent portable carrier device comprising a housing having storage compartment, a battery compartment, a processor compartment and a lid-closure mechanism, the housing being constructed of an RF absorptive material and configured such that any RF emitted energy within the housing does not emit outside the housing;

affixing a radio-frequency identification (RFID) tag to at least one regulated product initialized with at least a product ID code unique to the product type and a serial number unique to the at least one specific regulated product, the RFID tag comprising a biosensor configured to detect a condition of the storage compartment;

placing the at least one tagged regulated product into the storage compartment;

scanning the RFID tag with a scanning device comprising a RFID reader to determine the product ID code and serial number, the scanning device being configured to determine the condition of the storage component based upon signals from the RFID tag and to detect whether the at least one regulated product is currently in the storage compartment or has been added to or removed from the storage compartment based upon signals from the RFID tag;

receiving the scanned data from said scanner into a local processor, the processor positioned in the processor compartment;

transmitting said scanned data from said local processor through an electronic data network to a tracking server;

creating a data record on said tracking server to contain said scanned data;

providing a power fail circuit configured to detect a power failure condition of the device; and generating a power failure event code if the power fail circuit detects a power failure condition.

11. The method of claim 10, wherein the step of scanning the RFID tag with a scanning device to determine the product ID code and serial number is performed periodically.

12. The method of claim 10, wherein the RFID continuously monitors the condition of the storage compartment.

13. The method of claim 12, wherein the condition of the storage compartment is temperature.

14. The method of claim 10, further comprising a step of generating an event-identifying code in response to detecting that a tagged regulated product has been added to or removed from a compartment of the intelligent portable carrier device which houses the regulated products.

15. The method of claim 14, further comprising storing the event-identifying code in an internal memory associated with a processor of the intelligent portable carrier device.

16. The method of claim 10, further comprising a step of generating an environmental condition change related code in response to a change in the condition of the storage compartment.

17. The method of claim 10, wherein the step of transmitting said scanned data from said local processor through an electronic data network to a tracking server comprises wirelessly transmitting said scanned data to a server of an existing back-end inventory tracking system via a transceiver of the intelligent portable carrier device.

18. The method of claim 10, further comprising receiving signals from a global positioning system and determining a location of the intelligent portable carrier device from the received signals.

19. The method of claim 10, wherein generating the power failure event code comprises determining a starting time of the power failure condition and then storing the power failure event code and the starting time of the power failure condition.

20. An intelligent portable carrier device comprising a housing including a lid-closure mechanism, a storage compartment, a battery compartment and a processor compartment, the housing being constructed carbon fiber and is configured such that any RF emitted energy within the housing does not emit outside the housing, the storage compartment comprising a plurality of regulated products disposed therein, the regulated products being selected from a group consisting of sterile implants and biologics, the regulated products each comprising a read-write radio-frequency identification tag coupled thereto, the tags each comprising a biosensor configured to detect a temperature of the storage compartment, the device comprising a RF reader in the processor compartment configured to collect, decode and pass on information relating to the temperature of the storage compartment based upon signals from the tags and to detect whether each of the regulated products is currently in the storage compartment or has been added to or removed from the storage compartment based upon signals from the tags.

* * * * *

UNITED STATES PATENT AND TRADEMARK OFFICE
CERTIFICATE OF CORRECTION

| | | |
|---|---|---|
| PATENT NO. | : 9,307,756 B2 | Page 1 of 1 |
| APPLICATION NO. | : 13/281588 | |
| DATED | : April 12, 2016 | |
| INVENTOR(S) | : Clement et al. | |

It is certified that error appears in the above-identified patent and that said Letters Patent is hereby corrected as shown below:

On the Title Page, in Item (73), under "Assignee", in Column 1, Line 2, delete "(IN)" and insert -- IN (US) --, therefor.

Specification

In Column 3, Line 35, delete "RFD" and insert -- RFID --, therefor.

In Column 5, Line 46, delete "include." and insert -- include --, therefor.

In Column 7, Line 23, delete "RFD" and insert -- RFID --, therefor.

In Column 9, Line 28, delete "COMA" and insert -- CDMA --, therefor.

Signed and Sealed this
Twelfth Day of July, 2016

Michelle K. Lee
*Director of the United States Patent and Trademark Office*